Sept. 19, 1950 F. W. ANDERSON Plant Pat. 980
NECTARINE TREE
Filed Oct. 7, 1949
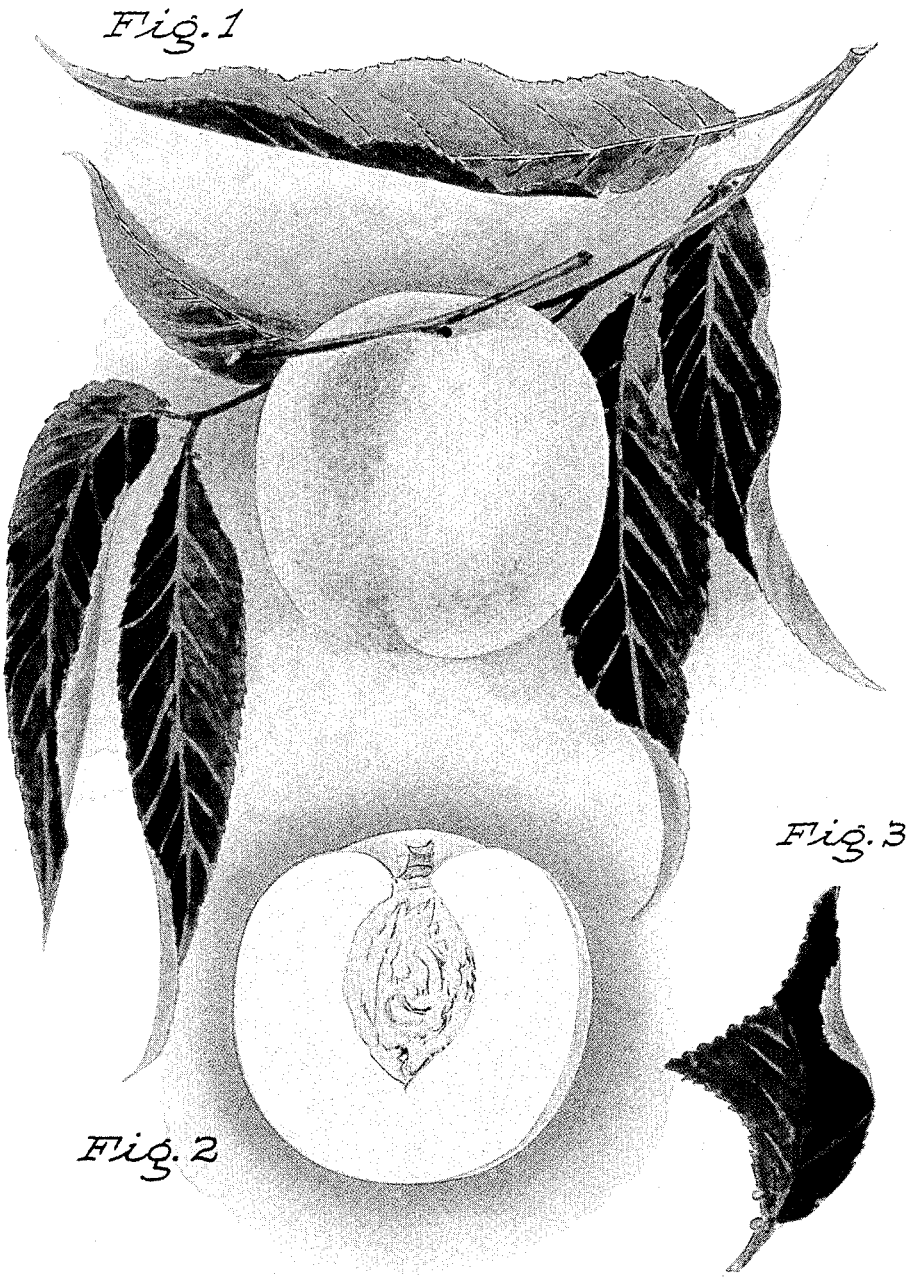
WITNESS
Addison J. Avery
INVENTOR
F. W. Anderson
Webster & Webster
ATTYS.

Patented Sept. 19, 1950

Plant Pat. 980

UNITED STATES PATENT OFFICE

980

NECTARINE TREE

Frederic W. Anderson, Merced, Calif.

Application October 7, 1949, Serial No. 120,108

1 Claim. (Cl. 47—62)

The present invention relates to a new and distinct variety of nectarine tree which bears yellow fleshed clingstone fruit; the variety being a result of a long-time selective breeding program which I have carried forward to obtain more commercially desirable nectarines.

The herein described variety of nectarine tree has close resemblance to the Le Grand nectarine (United States Plant Patent No. 549), but the present variety is distinctive in comparison thereto in that it has a ripening period which is approximately three weeks earlier.

This new and distinct variety of nectarine tree was originated by me upon my ranch near Merced, county of Merced, State of California, in the following manner:

Several thousand seeds of the Le Grand nectarine were planted in 1942 and allowed to come into bearing in a nursery row. Among these seedlings, which were open-pollenated, there appeared the instant variety, and which was recognized by me as distinctive by reason of its ripening period some three weeks earlier than the parent Le Grand.

The variety thus originated as an open-pollenated seedling of the Le Grand variety, and subsequently was top worked on mature orchard trees at my ranch located as aforesaid. These top worked trees have now come into bearing and the asexual reproductions are found to retain in full the novel characteristics of the parent tree.

The ripening period, during the 1948 season, was the first week in July as compared to the Le Grand nectarine which ripened during the last week of such month.

The ripening period of the present variety may be further compared as follows:

The present leading varieties of nectarines in California, all of which are grown by me, are—in the order of their ripening—John Rivers; Gower; Quetta; Stanwick; and the commercially important yellow fleshed varieties Bim (United States Plant Patent No. 575); Kim (United States Plant Patent No. 173); and Le Grand (United States Plant Patent No. 549).

As compared to the well known Elberta peach, the above seven varieties ripen as follows:

John Rivers—6 weeks before Elberta (approximately 43 days)

Gower—2 weeks before Elberta (approximately 13 days)

Bim—1 week before Elberta (approximately 10 days)

Kim—1 week before Elberta (approximately 8 days)

Le Grand[1]—½ week before Elberta (approximately 4 days)

Quetta—½ week before Elberta (approximately 4 days)

Stanwick—2 weeks after Elberta (approximately 13 days).

In relative comparison to the above the present variety ripens approximately twenty-five days before the Elberta peach, thus having a first picking approximately three weeks earlier than the Le Grand; about the same time that the John Rivers harvest is completed; and about ten days before the Gower harvest begins.

While the John Rivers and Gower varieties of nectarines are relatively small and white fleshed, the present variety has yellow flesh and averages at least fifty percent (50%) larger in fruit size, being very similar to the Le Grand with respect to fruit size, color, and shape.

In the drawings:

Fig. 1 is a perspective view of one of the fruit on a twig, and in association with leaves of the variety.

Fig. 2 is a sectional view of the fruit taken axially thereof and with the stone exposed.

Fig. 3 is a fragmentary elevation of one of the leaves, showing particularly the glands.

Referring now specifically to the new and distinct variety of nectarine tree, the following is a detailed description thereof in outline; all color plate identifications being by reference to Maerz and Paul Dictionary of Color.

Tree: Large size, vigorous, spreading, productive, regular bearer.

Trunk: Stocky.

Branches: Above medium size, stocky. *Lenticels*—medium length, medium thickness.

Leaves: Large size; average length—6 to 7 inches; average width—1¾ to 2 inches. Smooth. Color—medium green (top side 22–L–9; under side 22–K–7).

*Margin.*—Crenate.

*Petiole.*—Medium length, medium thickness.

*Glands.*—Average four in number; alternate, medium size, reniform. Located two on the petiole and two or more on the margins of the blade. No stipules.

[1] The Le Grand nectarine, which the present variety most resembles, ripens more nearly with the J. H. Hale peach; viz, picking begins three or four days before the Elberta, and extends from four to eight days after the latter.

Flower buds: Medium size, plump.
Flowers: Large size, showy.
*Color.*—Pink.
*Blossom period.*—About with Elberta peach.
Fruit:
*Size.*—Extremely large for a nectarine, being larger than any commercially grown nectarine except Le Grand. Well grown specimens average three inches in ring diameter and slightly more from stem to apex, being somewhat variable.
*Shape.*—Globose to oblong.
*Suture.*—Shallow with a marked depression beyond the pistil point.
*Ventral surface.*—Rounded and with lips equal.
*Cavity.*—Rounded, approximately ⅜'' in diameter and ¾'' in breadth, and usually marked with red lines.
*Base.*—Rounded.
*Apex.*—Depressed, with pistil point almost lacking.
*Stem.*—Stout—and adheres strongly to stone (like the J. H. Hale).
Skin: Above medum in thickness; above medium in toughness; tenacious to the flesh.
*Color.*—Yellow (10–L–6), overspread with red (5–L–8).
*Pubescence.*—None.
Flesh: Yellow (10–K–7 shading into 11–L–8), streaked with red next to stone. Surface of pit cavity—red with yellow fibers.
*Amygdalin.*—Moderate.
*Fibers.*—Abundant.
*Juice.*—Abundant.
*Texture of flesh*—Very firm.
*Ripens.*—Evenly.
*Flavor.*—Delicate and somewhat acid.
*Aroma.*—Distinct.
*Eating quality.*—Very good to best.

Stone: Cling.
*Fibers.*—Long.
*Size.*—Large, averaging 1⅜'' in length, 1¼'' in breadth, and ⅝'' in thickness.
*Form.*—Oval.
*Base.*—Oblique.
*Hilum.*—Broad and oval.
*Apex.*—Rounded.
*Sided.*—Equal.
*Surface.*—Irregularly furrowed and pitted throughout.
*Ventral side.*—Thick.
*Dorsal edge.*—Full with deep grooves.
*Ridges.*—Continuous.
*Color.*—Reddish.
Some tendency toward splitting.
Resistance to insects and diseases: Medium.
Keeping and shipping quality: Very good, having firm flesh with uniform ripening comparable to the J. H. Hale peach or Le Grand nectarine.

The tree and its fruits herein described may vary in slight detail due to climatic and soil conditions under which the variety may be grown.

Having thus described my invention, I claim:

A new and distinct variety of nectarine tree, as shown and described, characterized by its close physical resemblance to the Le Grand nectarine including large clingstone fruit which is yellow blushed red exteriorly, and with firm yellow flesh, but having a ripening period approximately three weeks earlier than said Le Grand nectarine; such ripening period being about the end of the John Rivers harvest and about ten days before the Gower harvest.

FREDERIC W. ANDERSON.

REFERENCES CITED

The following references are of record in the file of this patent:

UNITED STATES PATENTS

| Number | Name | Date |
|---|---|---|
| Pl. Pt. 549 | Anderson | Oct. 13, 1942 |